(12) United States Patent
Pesenti et al.

(10) Patent No.: US 8,734,375 B2
(45) Date of Patent: May 27, 2014

(54) BLOOD TREATMENT METHOD ADAPTED TO AT LEAST PARTIALLY ELIMINATE THE CARBON DIOXIDE CONTENT AND RELATED DEVICE

(75) Inventors: Antonio Maria Pesenti, Milan (IT); Nicolò Antonino Patroniti, Milan (IT)

(73) Assignee: Universitá degli Studi di Milano-Bicocca (IT)

( * ) Notice: Subject to any disclaimer, the term of this patent is extended or adjusted under 35 U.S.C. 154(b) by 526 days.

(21) Appl. No.: 12/599,254

(22) PCT Filed: May 7, 2008

(86) PCT No.: PCT/EP2008/003661
§ 371 (c)(1), (2), (4) Date: Feb. 4, 2010

(87) PCT Pub. No.: WO2008/135282
PCT Pub. Date: Nov. 13, 2008

(65) Prior Publication Data
US 2010/0198132 A1    Aug. 5, 2010

(30) Foreign Application Priority Data
May 7, 2007   (IT) .............................. MI2007A0913

(51) Int. Cl.
*A61M 37/00*   (2006.01)
(52) U.S. Cl.
USPC ........................................ 604/6.14; 604/4.01

(58) Field of Classification Search
USPC .............................. 604/6.09, 6.14; 623/11.11
See application file for complete search history.

(56) References Cited

U.S. PATENT DOCUMENTS

| | | | | |
|---|---|---|---|---|
| 4,019,862 A | * | 4/1977 | Dahms | 436/68 |
| 5,914,130 A | * | 6/1999 | Whang | 424/466 |
| 6,029,076 A | * | 2/2000 | Fiddian-Greene et al. | 600/353 |
| 6,280,634 B1 | * | 8/2001 | Shah et al. | 210/739 |
| 6,869,938 B1 | * | 3/2005 | Schwartz et al. | 514/57 |
| 2005/0040029 A1 | * | 2/2005 | Monzyk et al. | 204/157.15 |
| 2005/0059669 A1 | * | 3/2005 | Ajito et al. | 514/252.13 |
| 2005/0082225 A1 | | 4/2005 | Kreymann | |
| 2005/0236329 A1 | | 10/2005 | Brotherton et al. | |
| 2006/0138049 A1 | * | 6/2006 | Kim et al. | 210/646 |
| 2008/0314385 A1 | * | 12/2008 | Brunner et al. | 128/204.23 |
| 2009/0123907 A1 | * | 5/2009 | Shanbrom | 435/2 |
| 2010/0010412 A1 | * | 1/2010 | Fava et al. | 604/5.04 |

FOREIGN PATENT DOCUMENTS

DE   4028311 C1 * 12/1991 ............... A61B 5/14
WO   2005/082504 A2   9/2005

* cited by examiner

*Primary Examiner* — Philip R Wiest
*Assistant Examiner* — Benjamin Klein
(74) *Attorney, Agent, or Firm* — Akerman LLP

(57) ABSTRACT

A blood treatment method is described that is adapted to at least partially eliminate the carbon dioxide content of the type comprising a step of drawing a blood flow. Advantageously according to the invention, the method further comprises the steps of: acidifying the blood flow with transformation of the related blood bicarbonate content into gaseous carbon dioxide; and eliminating the gaseous carbon dioxide content by means of a pressure gradient.

17 Claims, 3 Drawing Sheets

BLOOD TREATMENT METHOD ADAPTED TO AT LEAST PARTIALLY ELIMINATE THE CARBON DIOXIDE CONTENT AND RELATED DEVICE

FIELD OF APPLICATION

The present application refers to a blood treatment method adapted to at least partially eliminate the carbon dioxide content.

The invention also refers to a blood treatment device.

PRIOR ART

As it is well known, the lungs are very elastic organs, situated in the thoracic cavity, capable of expanding and contracting in order to introduce and expel air. In particular, each lung is formed by alveoli also called respiratory cells, since the gas exchange between the blood and the breathed air occurs therein, the related surface being vascularised by a great number of capillaries coming from the pulmonary artery.

The air that is breathed, through the respiratory pathways, then arrives at the pulmonary alveoli. Here the oxygen ($O_2$) passes via diffusion into the capillaries, binding itself to the haemoglobin, through the circulatory system, arriving at all body tissues. One of the final products of the chemical reactions occurring in the tissues, i.e. the carbon dioxide ($CO_2$), is meanwhile collected by the circulating blood and transported to the pulmonary capillaries, where it diffuses in the alveoli and then it is expelled during expiration, always through the respiratory pathways.

The body metabolism, in substance, consumes oxygen and produces carbon dioxide. Oxygen and carbon dioxide are then exchanged with the atmospheric air by means of the ventilation mechanism achieved by the lungs, where the blood is loaded with oxygen and gives up carbon dioxide.

These processes can be slowed to a fraction of the normal resting level (considered to be the reference level), e.g. by hypothermia, or accelerated up to 20 times the resting level when the metabolism increases, such as in the case of fever, hyperthermia or physical exertion.

The amount of air inserted and emitted in the lungs during a normal respiratory act is about 500 $cm^3$, but it can considerably increase.

Physiological mechanisms coupled and balanced by chemical buffer systems always maintain the oxygen/carbon dioxide exchange system in the lungs in equilibrium.

In numerous pathological conditions, however, the elimination of carbon dioxide through the lungs is altered, made difficult or in any case interferes with other physiological and/or therapeutic processes (such as artificial mechanical ventilation).

In such cases, it is known to employ a blood processing organ, in particular known as artificial lung, that can be utilised to assist a deficiency of the natural organ both for brief time periods or permanently, or even to substitute the entire pulmonary exchange function, if for example the natural organ is completely insufficient, or if, still healthy, it must be stopped for a limited time period, for example due to a surgical operation.

Currently, artificial lungs are achieved by means of relatively large devices, and cannot be placed in the anatomic site of the natural lungs. In particular, the venous blood is deviated from its normal course through the central veins and is redirected by means of catheters and tubes into an extracorporeal circuit comprising the artificial lung, so to be finally returned—by means of a pump—to the arterial system, thus avoiding heart and lungs.

The interruption of the pulmonary circulation and the use of an artificial lung for surgical applications is often indicated as an extracorporeal circulation, since in operating rooms, the device for the gas exchange and the pump which makes the blood circulate are placed outside the body.

In particular, the venous blood, excluded from the lung circuit, comes to be artificially oxygenated by means of a gas exchanger, in particular an oxygenator.

The oxygenator is only a part of a great veno-arterial-cardiopulmonary circuit that takes the name of heart-lung machine. In particular, in such a machine, all of the venous blood, which returns towards the right atrium of the heart, is collected in an extracorporeal circuit, pumped into an oxygenator from which it is conveyed into the arterial circuit, thus avoiding the heart and the pulmonary circuit.

During this process, the blood is heparinised in order to avoid the formation of thrombi and its temperature is lowered several degrees in order to reduce oxygen consumption by the main organs, while oxygen, or a mixture of gas rich in oxygen, flows from a moderately pressurised source in a continuous manner and without recirculation.

The main problem encountered in making an oxygenator that acts as an artificial lung is the creation of a large surface for gas-blood exchange. This problem is resolved in the prior art using a membrane oxygenator, by making blood and gas flow along opposite faces of a gas permeable membrane.

The currently available equipment thus operates on the carbon dioxide amount dissolved as gas in the blood, which in reality is a limited portion of the total carbon dioxide content of the blood.

In fact, in all membrane exchangers, the gases are moved from the higher partial pressure compartment towards the lower one. In the case of carbon dioxide, this is moved from the side of the biological liquids (blood, plasma, ultrafiltrate, etc.) towards that of the ventilation fluid, moved by a relatively small pressure gradient. Only very rarely and in seriously pathological conditions, the body carbon dioxide pressure naturally exceeds 80 mmHg, while the carbon dioxide pressure of the ventilation fluid can never be less than 0 mmHg. There is therefore a pressure gradient physiologically limited to a value equal to 5-10% of the atmospheric pressure.

It is therefore necessary to treat a large amount of blood in order to eliminate a carbon dioxide amount such as to maintain constant its level in the blood, notwithstanding the continuous production by the body metabolism. In particular, it is known that a man of medium build of 70 Kg produces carbon dioxide in an amount equal to about 10 mMol/min: this is therefore the amount that a membrane oxygenator must eliminate, in practice necessitating the treatment of about 1.5-2.5 liters/min of blood. This is the objective in the case of the so-called "Total CO2 Removal", with the possibility of a complete apnoea for an indeterminate time, i.e. total substitution of the natural respiratory function.

The involved amounts of blood to be treated require the use of machines and procedures that are particularly invasive, which limit their use to heart surgery operations or to extremely serious situations, as a last resort for preventing death.

Moreover, the patient must be connected to such machines at important vessels of the body, by means of semi-permanent implants that cannot be compared to the cannulas currently used for example in the case of dialysis, with a considerable risk of major complications, even death, for the patient.

Finally, the high volume of treated blood increases the risks of damage to its corpuscular parts, obliging the patient to follow appropriate support therapies.

The technical problem underlying the present invention is that of providing a treatment method of the blood, and related device, that permits reducing the carbon dioxide content of the treated blood, reducing the blood flows and volumes necessary for obtaining a partial or total substitution of the natural ventilation mechanism, in such a manner overcoming the limitations and drawbacks that still limit the devices made according to the prior art.

SUMMARY OF THE INVENTION

The solution idea underlying the present invention is that of acting on the carbon dioxide portion in the blood in bicarbonate form, such portion being much greater than the one dissolved as gas.

On the basis of such solution idea, the technical problem is solved by a treatment method of the blood adapted to at least partially eliminate from it the carbon dioxide content of the type comprising a step of drawing a blood flow and characterised in that it further comprises the steps of:
  acidifying said blood flow with transformation of the related blood bicarbonate content into gaseous carbon dioxide; and
  eliminating said gaseous carbon dioxide content by means of a pressure gradient. An extracorporeal blood treatment is thus obtained.

Advantageously, according to the invention, said acidifying step comprises a step of inserting an acid load.

Further advantageously, the method also comprises a step of removing said acid load from said acidified blood flow with the obtainment of a treated blood flow, as well as a step of ventilating simultaneous with said acidification step and a possible step of oxygenating said blood flow through an artificial membrane lung.

Appropriately, said insertion step of said acid load provides for an inflow of a mixture of organic and inorganic acids in various proportions and total amount.

Advantageously according to the invention, the treatment method of the blood can comprise a preliminary step of filtering said blood flow, said acidification step being made on an ultrafiltrate thus obtained.

Further advantageously, the method comprises a recirculation step of said blood flow in a feedback path, with insertion of a treated blood portion to said blood flow immediately following said acidification step. The method according to the invention also comprises, in said step of removing said acid load, a step of hydroelectrolytic rebalancing, achieved in one of the following methods:
  direct haemodialysis of said treated blood flow;
  filtration of said treated blood flow, with obtainment of an ultrafiltrate and elimination of an ultrafiltrate amount such to compensate for said inserted acid load, with subsequent infusion of a basic load amount;
  balancing, via dialysis or electrodialysis, of an ultrafiltrate possibly with a batch liquid subjected to desalination, with a subsequent infusion of a basic load amount if required;
  balancing of an ultrafiltrate via electrodialysis or diffusion dialysis with net removal of the added acid load and possible reutilization of the same for blood acidification.

The problem is also solved by a blood treatment device adapted to at least partially eliminate the carbon dioxide content of the type comprising at least one inlet terminal for inflow of a blood flow and an outlet terminal for outflow a treated blood flow characterised in that it comprises at least one acidification stage and one gas exchanger inserted, in series with each other, between the inlet and outlet terminals, said gas exchanger eliminating the gaseous carbon dioxide content of said venous blood flow acidified by said acidification stage.

Advantageously according to the invention, said acidification stage is adapted to insert an acid load in said venous blood flow with obtainment of an acidified blood flow that is inserted into said gas exchanger, which ventilates it.

Further advantageously according to the invention, a deacidification stage is inserted downstream of said gas exchanger, in order to supply said treated blood flow at said outlet terminal.

Suitably, said gas exchanger is a membrane oxygenator adapted to eliminate, via pressure gradient, the gaseous carbon dioxide content from said acidified gas flow and possibly to oxygenate it, giving rise to a decarbonised and possibly oxygenated blood flow, still acidified, sent to said deacidification stage.

Further advantageously according to the invention, said deacidification stage is adapted to remove the acid load by means of elimination of anions with inflow of a basic load to said decarbonised and possibly oxygenated blood flow with obtainment of a treated blood flow, supplied to said outlet terminal.

The device according to the invention further comprises a recirculation block adapted to draw, in a feedback path, a portion of said decarbonated blood downstream of said gas exchanger and to mix it with said acidified blood flow in order to lower the blood pH upstream of said gas exchanger.

In an advantageous alternative embodiment, the device further comprises a haemofilter for producing an ultrafiltrate, appropriately connected upstream of said acidification stage or inserted between said acidification stage and said gas exchanger or also connected downstream of said gas exchanger.

Said haemofilter is also advantageously inserted in said feedback path with said recirculation block.

The features and advantages of the method and device of blood treatment according to the invention will be clearer from the following description, made hereinbelow, of an embodiment thereof given as indicative and non-limiting example with reference to the attached drawings.

DETAILED DESCRIPTION

Figure 1:
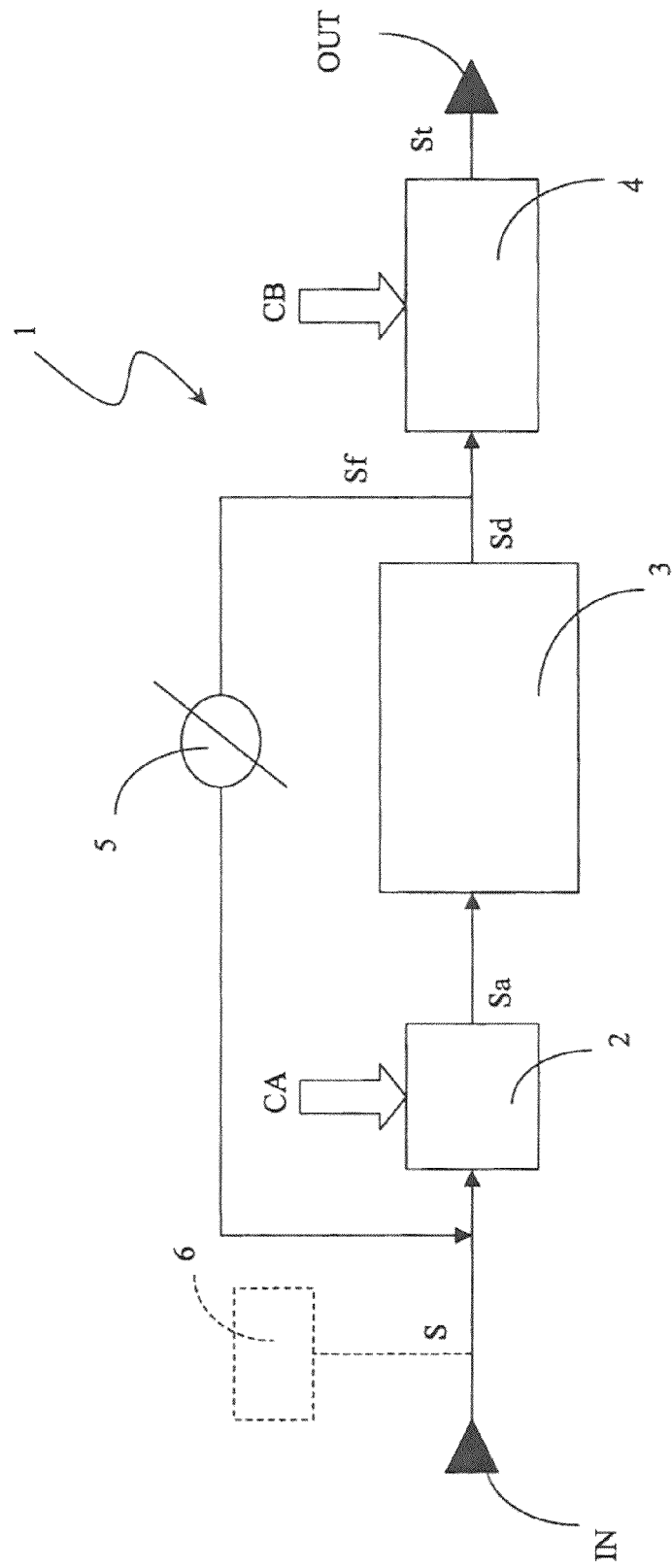
FIG. 1 schematically shows a blood treatment device adapted to implement the method according to the invention.

First of all, it is opportune to underline the fact that the present invention primarily arises from the consideration that carbon dioxide is transported in the blood according to two principal mechanisms:
  dissolved as a gas; as in a bicarbonate ion form
and from the fact that the carbon dioxide portion present as a bicarbonate ion is much greater than the amount dissolved as a gas.

Starting from such considerations, advantageously according to the invention, a blood treatment method is proposed for eliminating the carbon dioxide by means of a conversion of its portion present as a bicarbonate ion, indicated below as blood bicarbonate.

In particular, advantageously according to the invention, the method comprises a reaction step of such blood bicarbonate and its transformation into gaseous carbon dioxide, which is then eliminated by means of a simple pressure gradient.

It should be recalled that a similar mechanism is used in natural ventilation, i.e. by the lungs, where an enzyme, in particular carbon anhydrase, permits the reaction of the blood bicarbonate and its transformation into gas, normally a very slow reaction.

It is also underlined that such chemical reaction with transformation of the blood bicarbonate into gaseous carbon dioxide liberates an amount of gas that is absolutely within the capacity of a normal membrane oxygenator, whose effectiveness is limited in known equipment only by the reduced carbon dioxide amount already present in gaseous form.

Furthermore, it is underlined that the partial pressure of carbon dioxide at the time of the transformation of the blood bicarbonate into gaseous carbon dioxide increases up to ten times, thus proportionately increasing the carbon dioxide elimination capacity of the employed membrane oxygenator.

More in detail, the blood treatment method according to the invention comprises the following fundamental steps:
  acidifying the blood with transformation of the blood bicarbonate into gaseous carbon dioxide; and
  eliminating the gaseous carbon dioxide content.

An extracorporeal blood treatment is thus obtained.

Advantageously according to the invention, the blood acidification step comprises a simultaneous ventilation of the same. During such ventilation step, an oxygenation step of the blood flow is also provided.

In addition, the method comprises a final step for removing the acid load remaining in the blood. It is thus possible to reinsert the treated blood (in particular cleaned of its carbon dioxide content, oxygenated and purified of the acid load) in the patient.

Advantageously according to the invention, the step of acidifying the blood comprises a step for inserting an acid load (in particular an anionic load) in the blood, more in particular a mixture of an inorganic acid in various proportions and total amount, such as hydrochloric acid HCl, and organic acids, such as pyruvic acid, citric acid and lactic acid (already normally existing and metabolized in the organism). More in detail, one such acid mixture is inserted in an amount normally in the range of 0-10 mMol/min in the blood as drawn from a patient, typically venous blood that returns towards the right atrium of the heart loaded with carbon dioxide and poor in oxygen.

In such a manner, for a blood flow for example of 400 ml/min that, as will be clear in the following description, is sufficient for ensuring the desired elimination of carbon dioxide for a total substitution of the natural ventilation, a maximum addition (under normal conditions) of about 25 mMol/liter of acid load is considered.

It can be immediately verified that the addition of such maximum acid load converts nearly all of the blood bicarbonate, i.e. the bicarbonate ion contained in the blood bound to the water (equal to about 25 mMol/litro) into gaseous carbon dioxide or carbonic acid.

The partial pressure of gaseous carbon dioxide obtained by the above-indicated reaction reaches values greater than 450 mmHg. It is opportune to emphasize the fact that, even in closed environments (i.e. non-ventilated environments), such pressure values are in any case secure, since they do not lead to the formation of bubbles or micro-bubbles.

It is also verified that, following the addition of the acid load in the above-indicated proportions, the blood pH value or haematic pH would be as low as approximately 5.7, a very dangerous value for the survival of the red corpuscles and other blood cells. Advantageously according to the invention, the ventilation step of the blood flow is therefore provided, in particular by using a membrane oxygenator, bringing the gaseous carbon dioxide pressure to values of 5-20 mmHg and the blood pH to nearly normal values.

Membrane oxygenator, thanks to the high partial pressure of the carbon dioxide thus generated, in this manner nearly completely eliminates the gaseous carbon dioxide content of the acidified blood.

It should be noted that the acidification step of the blood or of the ultrafiltrate raises considerably the carbon dioxide pressure, favouring its removal towards a gaseous phase at a lower carbon dioxide pressure, i.e. towards an employed ventilation gas.

Appropriately, the membrane oxygenator also achieves the desired oxygenation step of the blood.

In a preferred embodiment of the invention, in order to avoid locally sharp drops of the blood pH as well as local accumulations of gaseous carbon dioxide, the method comprises a preliminary step of ultrafiltration of the blood, with separation of its corpuscle part from the plasma or ultrafiltrate (as will be better explained in the following description with reference to FIG. 2).

In such a case, the acidification step of the blood provides for the addition of the acid load to the ultrafiltrate, which is reinserted in the system upstream of the gaseous exchanger and ultrafiltrate.

It is also possible (as will be explained better in the following description with reference to FIG. 4) to provide for a step of feedback recirculation of the blood flow, with inflow of an already ventilated and further acidified blood flow portion coming from the patient, in such a manner limiting the variation of the blood pH.

Further advantageously according to the invention, the method then provides for a step of removing the acid load from the treated blood. Considering that the organic acid part of the acid mixture (which in any case should not exceed about 1 mMol/min, and thus can correspond in the case of total removal from 10% to 30% of the total acid load) is removed by the treated patient's metabolism, in order to avoid a rapid acidosis of the patient, the removal step should involve the removal of the non-metabolisable or inorganic acid load added to the blood.

In a preferred embodiment of the method according to the invention, the removal step of the acid load of the treated blood, in particular decarbonised blood, comprises a step of hydroelectrolytic rebalancing. Further advantageously, where the elimination of acid anions is accompanied by a loss of cations, these are supplied to the patient, also in the form of bases (hydroxides).

It is possible to achieve, in a simple manner, such hydroelectrolytic rebalancing step of the treated blood by means of its direct haemodialysis before its reinsertion.

In this case, it is necessary to consider that, in particular in the case of total or near-total removal of carbon dioxide, it is possible to reach very alkaline pH values, harmful for the red corpuscle, and which could cause calcium precipitation.

It is also possible to consider a step of removing the acid load comprising the steps of:
- filtering the treated blood (in particular by means of a haemofilter) with obtainment of an ultrafiltrate (usually equal to 70-100 ml/min);
- eliminating or discarding an ultrafiltrate amount such as to compensate for the addition of the acid load, in particular eliminating a corresponding level of acid ions (CL−); and
- subsequent infusion of a basic load amount in an appropriate region, in particular a mixture of inorganic bases, including $NaOH$, $KOH$, $Mg(OH)_2$, $Ca(OH)_2$ and other positive ions, suitable for re-establishing the content of cations of the blood that have been lost with the ultrafiltrate.

It can be immediately verified that the ultrafiltrate obtained from the treated blood will have a load of anions (acids) of approximately 130 mEq/liter and it is therefore possible to calculate the ultrafiltrate amount to eliminate in order to rebalance the acid content on the basis of the added acid load.

In particular, it is known that the blood ultrafiltrate has an electrolytic content approximately equal to that of the plasma, with increase of the anion content (Cl— and HCO3-) due to the lack of protein in the ultrafiltrate phase. For example, if 5 mEq/minute of HCl acid are infused (for a removal of between 50% and 100% of the carbon dioxide production) it will suffice eliminating between 40 and 50 ml/min of ultrafiltrate in order to maintain constant the bodily content of acid ions (CL−). It is also necessary to infuse a basic load, in particular a solution which contains positive ions (Na, K, Mg and Ca) in hydroxide form, in order to maintain constant the concentration of these latter.

It should also be noted that this basic load infusion can appropriately occur in a different path from that of the blood re-insertion, possibly in a central vein.

The hydroelectrolytic rebalancing ultrafiltration can be carried out before or after the acidification step, if before eliminating also a bicarbonate portion.

Alternatively, it is possible (and appropriate, above all if the total removal of carbon dioxide is carried out) to balance, directly or through dialysis, the ultrafiltrate according to one of the known hydroelectrolytic rebalancing methods, including reverse osmosis, electrodialysis, passage on a column with basic ion exchange, diffusion or electro-dialysis through ion exchange membrane . . . (in the latter case with acid recovery and possible reinfusion).

Moreover, the obtainment of an intermediate ultrafiltrate rather than the direct treatment of the blood is suggested by the need to prevent the blood from reaching very high pH values.

It is easily verified that the proposed method can effectively eliminate nearly all of the carbon dioxide content of the blood. It will suffice to treat between 350 and 450 ml/min of blood in order to obtain a near total removal of the production/minute of carbon dioxide and thus permit the substitution of the natural ventilation.

According to advantageous reaction variants, the blood treatment method according to the invention comprises more than one step of acidifying the blood with insertion of several acid loads, so to eliminate greater amounts of carbon dioxide with chain transformations of the blood bicarbonate into gaseous carbon dioxide. It is also possible to consider several blood ventilation steps.

The blood treatment method according to the invention can appropriately comprise pumping steps of the blood flow and/or ultrafiltrate.

The blood treatment method according to the invention is carried out by the blood treatment device schematically illustrated in FIG. 1, generally indicated with 1.

In particular, the blood treatment device 1 comprises an inlet terminal IN for the inflow of a blood flow S and an outlet terminal OUT for the outflow (i.e. return to the patient) of a treated blood flow St, in particular with elimination of the carbon dioxide content and possibly insertion of oxygen.

Advantageously according to the invention, the blood treatment device 1 comprises an acidification stage 2, a gas exchanger 3 and a deacidification stage 4.

More in detail, the blood flow S enters into the acidification stage 2, where it receives an acid load CA, transforming it into an acidified blood flow Sa that is inserted into the gas exchanger 3.

As seen above, the gas exchanger 3 is essentially a membrane oxygenator that eliminates the gaseous carbon dioxide content from the acidified blood flow (and possibly oxygenates it), giving rise to a decarbonised and possibly oxygenated blood flow Sd, still acidified.

The decarbonised blood flow Sd is then inserted into the deacidification stage 4 where the acid load present therein is eliminated with outflow of the treated blood flow St, such treated blood lacking carbon dioxide and the non-metabolisable portion of the acid load, and is then ready to be re-inserted into the patient. In particular, in the deacidification stage 4, it receives a basic load CB to add to the decarbonised blood flow Sd exiting from the gas exchanger 3. Such base load can be appropriately infused in any other infusion line of the patient, so to avoid, depending on the use conditions, excessive pH changes of the treated blood.

In a preferred embodiment of the invention, the blood treatment device 1 also comprises a recirculation block 5 adapted to draw—in a feedback path—a portion Sf of the decarbonised blood flow Sd and mix it with the blood flow coming from the patient S before acidification in order to limit sharp drops of the blood pH, as explained above with reference to the blood treatment method according to the invention.

According to an alternative embodiment, the blood treatment device 1 also comprises a haemofilter 6 for the ultrafiltrate production. Such haemofilter 6 can be upstream of the acidification stage 2, as illustrated in FIG. 1, or between the acidification stage 2 and the gas exchanger 3 or even downstream of the gas exchanger 3, before the deacidification stage 4, depending on the treatment variants described above with reference to the method according to the invention.

Of course, the blood treatment device 1 can be made with a series of elements or blocks adapted to implement the different steps of the method, as described above, separately optimised for carrying out the step assigned to them, or by means of an integrated device suitable for achieving all the required blood treatment steps.

Figure 2:
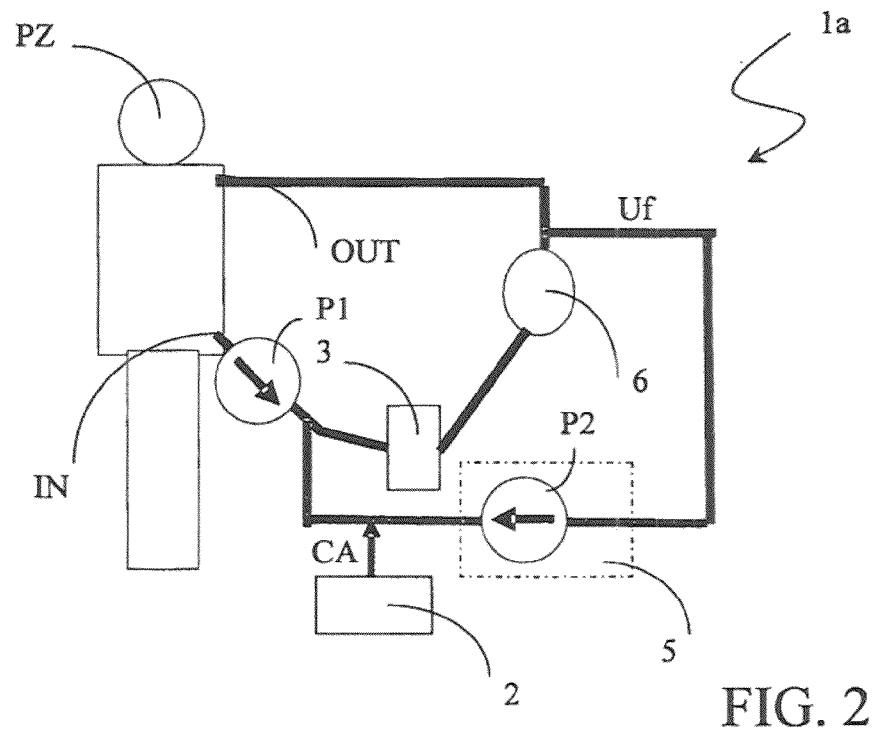
FIG. 2 schematically shows a first alternative embodiment of the blood treatment device according to the present invention.

In FIG. 2, a first alternative embodiment of the blood treatment device is schematically illustrated, indicated with 1a, suitable for making an acidification of an ultrafiltrate recirculating through a membrane exchanger in veno-venous, or arterial-venous, or veno-arterial bypass.

In particular, the blood treatment device 1a is connected to a patient PZ at a body vessel (connected to the inlet terminal IN of the device) and reinserted at the outlet terminal OUT of the device.

According to this first alternative embodiment, the blood is drained from the patient PZ by a first pump P1 and crosses a gas exchanger 3, in particular a membrane exchanger and then a haemofilter 6.

An ultrafiltrate Uf is thus obtained, which is acidified with an acid load CA, in particular with a mixture of physiological and inorganic acids, and reinserted in circulation upstream of the gas exchanger 3 by a second pump P2, which realises the circulation block 5. The blood treatment device 1a therefore comprises a feedback path including the second pump P2 adapted to realise the recirculation block 5 of a portion of the ultrafiltrate Uf and the acidification stage 2, adapted to insert the acid load CA into the drawn ultrafiltrate portion Uf.

A portion or level of ultrafiltrate UF is advantageously continuously discarded, so to maintain the bodily acid content constant, the volume substituted with a solution of bases as described above. Thus, the hydroelectrolytic rebalancing step of the treated blood is achieved.

This first alternative embodiment of the blood treatment device 1a according to the invention is particularly preferable in case of partial substitution of the natural ventilation function.

Figure 3:
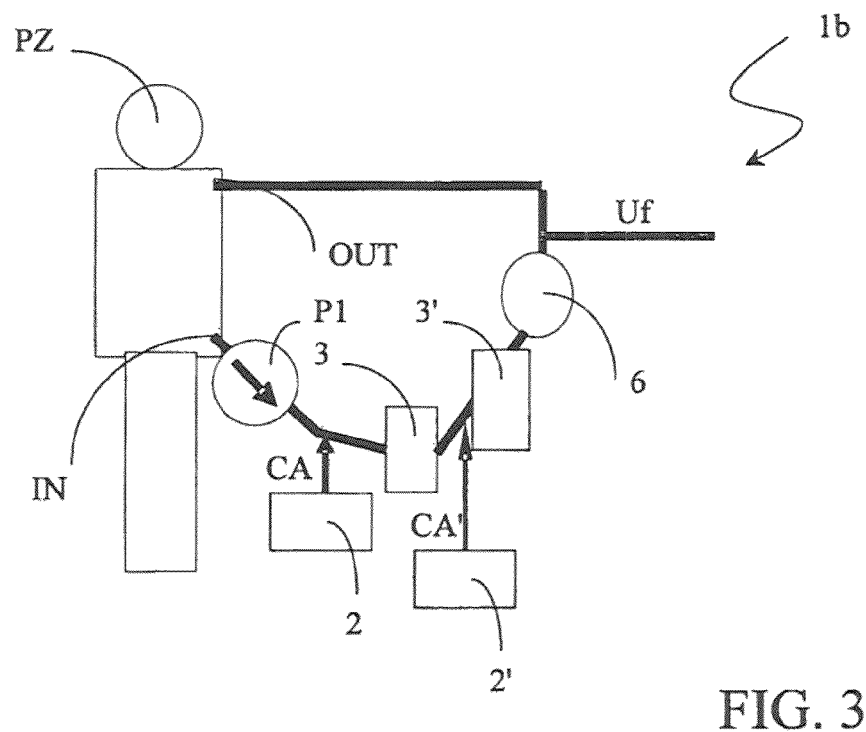
FIG. 3 schematically shows a second alternative embodiment of the blood treatment device according to the present invention.

In FIG. 3, a second alternative embodiment of the blood treatment device is schematically illustrated, indicated with 1b, adapted to achieve a direct acidification of the blood, a ventilation through a gaseous exchanger with subsequent stages and a final elimination of the acid load.

Also in this case, the blood treatment device 1b is connected to a patient PZ at a body vessel (connected to the inlet terminal IN of the device) and reinserted at the outlet terminal OUT of the device.

According to this second alternative embodiment, the blood is drained from the patient PZ by a first pump P1 and is acidified with a first acid load CA at a first acidification stage 2 before being sent to a first gas exchanger 3, in particular a membrane exchanger, where it is ventilated.

The acidified and ventilated blood is then newly added with a second acid load CA' at a second acidification stage 2', in such a manner increasing the carbon dioxide pressure. The blood is then newly ventilated by means of a second gas chamber 3'.

The number of acidification and gas exchange stages can be increased or reduced depending on the carbon dioxide removal needs.

The blood finally passes into a haemofilter 6 where a drawing of ultrafiltrate Uf occurs in order to achieve the hydroelectrolytic rebalancing step of the treated blood.

Figure 4:
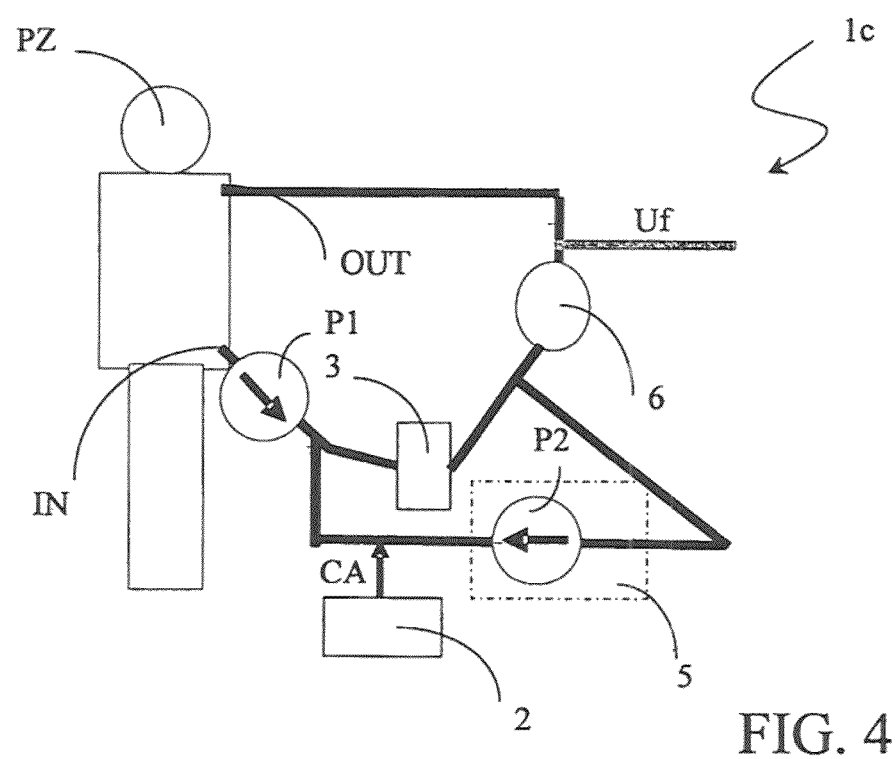
FIG. 4 schematically shows a third alternative embodiment of the blood treatment device according to the present invention.

In FIG. 4, a third alternative embodiment of the blood treatment device is schematically illustrated, indicated with 1c, suitable for achieving an acidification and a ventilation through a gaseous exchanger with blood recirculation.

Also in this case, the blood treatment device 1c is connected to a patient PZ at a body vessel (connected to the inlet terminal IN of the device) and reinserted at the outlet terminal OUT of the device.

According to this third embodiment, the blood is drained from the patient PZ by a first pump P1 and is recirculated at high flow into a circuit that comprises an acidification stage 2 for the inflow of the acid load CA and a gas exchanger 3 with blood recirculation achieved by a second pump P2 of the recirculation block 5 and final passage in the haemofilter for the drawing of ultrafiltrate Uf adapted to achieve the hydroelectrolytic rebalancing step of the treated blood. The blood treatment device 1c therefore comprises a feedback path including the second pump P2 adapted to realise the recirculation block 5 of a blood flow portion and the acidification stage 2, adapted to insert the acid load CA into the drawn portion of the blood flow.

The advantage of this third alternative embodiment of the blood treatment device is the low resistance, at the expense of a higher mechanical complexity (in particular with the need of two blood pumps).

In conclusion, advantageously according to the invention, the blood treatment method and device carry out an elimination of the related carbon dioxide content such to permit a substitution of the natural ventilation, even if treating limited blood amounts.

In particular, the blood treatment method according to the invention provides for a continuous passage of blood in the treatment device (this is therefore an extracorporeal treatment of the blood) and, by exploiting chemical-physical reaction mechanisms with an acid load, it achieves the transformation of the blood bicarbonate into gaseous form and permits its subsequent near-total elimination.

In substance, due to the liberation of the carbon dioxide contained in the blood flow in blood bicarbonate form, it permits the treatment of limited blood flows, in particular comparable to the blood flows required for kidney dialysis treatment, with substantial improvement of the benefit-risk profile of the extracorporeal removal treatment of the carbon dioxide. This technology can advantageously be applied to acute respiratory insufficiency (known as ALI/ARDS, acronym of Acute Lung Injury and Acute Respiratory Distress Syndrome, respectively), since it can eliminate the need for mechanical ventilation and its dangers. Potential, important applications, with incalculable effects on the improvement of the quality of life of the treated patients, can also be foreseen for those suffering from chronic respiratory insufficiency, or in any case for all the pathologies in which it is necessary to eliminate or reduce the ventilation need.

As indicated above, advantageously according to the invention, it is possible to eliminate from the body the entire carbon dioxide amount produced every minute, by treating even only 400-500 ml of blood (or other body fluid, the carbon dioxide content also being in any case high in the plasma or ultrafiltrate), instead of the 1.5 and 2.5 liters per minute of blood currently necessary for obtaining the objecting of the so-called "Total Co2 Removal".

In other words, by using the method according to the invention, it is possible to eliminate the need for mechanical ventilation, or even the need to breath through the natural lungs, with a technology equipped with an invasiveness and complexity entirely comparable to that of a normal haemodialysis.

Of course, the same advantage is obtained when only portions of the carbon dioxide production/minute are to be eliminated. For example, with only 200 ml of blood one eliminates about 50% of the carbon dioxide production, permitting to halve the natural ventilation need, in the case of partial deficiency of the respiratory apparatus.

Of course, a man skilled in the art, in order to satisfy contingent and specific needs, can make numerous modifications and variants to the above-described blood treatment method and device, all comprised in the protective scope of the invention as defined by the following claims.

The invention claimed is:

1. A blood treatment method adapted to at least partially eliminate the carbon dioxide content comprising the steps of:
   drawing a blood flow from a patient;
   acidifying said blood flow by inserting an acid load to cause transformation of the related blood bicarbonate content into gaseous carbon dioxide;
   eliminating said gaseous carbon dioxide content by means of a pressure gradient; and removing said acid load from said acidified blood flow, with obtainment of a treated blood flow, and returning said treated blood flow to the patient, wherein the acid load inserted into the blood flow comprises a mixture of an inorganic acid and organic acids and wherein said acidification step comprises a simultaneous step of ventilating said blood flow through an artificial membrane lung, in turn comprising a step of oxygenating said blood flow.

2. The blood treatment method according to claim 1, wherein said step of inserting said acid load provides for an inflow of a mixture of organic and inorganic acids in various proportions and total amount.

3. The blood treatment method according to claim 1, further comprising a step of filtering said blood flow and wherein said acidification step is achieved on an ultrafiltrate thus obtained.

4. The blood treatment method according to claim 3, wherein it provides for a step of pumping said ultrafiltrate.

5. The blood treatment method according to claim 1, further comprising a step of recirculating said blood flow in a feedback path, with inflow of a treated blood portion to said blood flow immediately before said acidification and ventilation step.

6. The blood treatment method according to claim 5, further comprising a step of recirculating said blood flow in a feedback path, with inflow of a blood portion that has been treated and further acidified immediately before its ventilation.

7. The blood treatment method according to claim 1, wherein said step of removing said acid load from said treated blood flow comprises a hydroelectrolytic rebalancing step.

8. The blood treatment method according to claim 7, wherein said hydroelectrolytic rebalancing step comprises one of the following methods:

direct haemodialysis of said treated blood flow;

filtration of said treated blood flow with obtainment of an ultrafiltrate and elimination of an ultrafiltrate amount such to compensate for said inserted acid load, with subsequent infusion of a basic load amount;

balancing, via dialysis, of an ultrafiltrate with a batch liquid subjected to desalination, with subsequent infusion of a basic load amount; or balancing of an ultrafiltrate via electrodialysis or diffusion dialysis with net removal of the added acid load and possible reutilization of the same for blood acidification.

9. The blood treatment method according to claim 1, wherein it comprises more than one blood acidification step with an inflow of several acid loads.

10. The blood treatment method according to claim 1, wherein it comprises several blood ventilation steps.

11. The blood treatment method according to claim 1, further comprising a step of pumping said blood flow.

12. The blood treatment method according to claim 1, wherein the inorganic acid is hydrochloric acid (HCl).

13. The blood treatment method according to claim 1, wherein the organic acids are selected from pyruvic acid, citric acid, and lactic acid.

14. The blood treatment method according to claim 1, wherein the acid mixture is inserted into the blood flow in an amount of less than about 25 mMol/liter.

15. The blood treatment method according to claim 1, wherein the acid mixture is inserted into the blood flow at a rate of 0-10 mMol/min.

16. The blood treatment method according to claim 1, comprising bringing the gaseous carbon dioxide pressure and the pH to nearly normal values.

17. The blood treatment method according to claim 1, comprising bringing the partial pressure of gaseous carbon dioxide to greater than 450 mmHg.

* * * * *